US00PP17980P3

(12) United States Plant Patent
Jepsen et al.

(10) Patent No.: US PP17,980 P3
(45) Date of Patent: *Sep. 4, 2007

(54) *KALANCHOE* PLANT NAMED 'JODIE'

(50) Latin Name: ***K. blossfeldiana*×*K. laciniata* *interspecific* hybrid**
Varietal Denomination: JODIE

(75) Inventors: Knud Jepsen, Hinnerup (DK); Ellen Christensen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 32 days.

This patent is subject to a terminal disclaimer.

(21) Appl. No.: 11/080,401

(22) Filed: Mar. 16, 2005

(65) Prior Publication Data

US 2006/0064792 P1 Mar. 23, 2006

(51) Int. Cl.
*A01H 5/00* (2006.01)

(52) U.S. Cl. ..... Plt./324
(58) Field of Classification Search ..... Plt./324, Plt./335
See application file for complete search history.

(56) References Cited

U.S. PATENT DOCUMENTS

| | | | | |
|---|---|---|---|---|
| PP12,299 | P2 | 12/2001 | Jepsen | |
| PP14,714 | P2 | 4/2004 | Vlielander | |
| PP13,365 | P2 | 12/2004 | Vlielander | |
| 2006/0041963 | A1 * | 2/2006 | Jepsen et al. | 800/323 |
| 2006/0041964 | A1 * | 2/2006 | Jepsen et al. | 800/323 |
| 2006/0130191 | A1 * | 6/2006 | Jepsen et al. | 800/323 |

OTHER PUBLICATIONS

UPOV ROM GTITM Computer Database, GTI Jouve Retrieval Software 2006/05 Citation for 'KJ20030818'.*

* cited by examiner

*Primary Examiner*—Kent Bell
(74) *Attorney, Agent, or Firm*—Foley & Lardner, LLP

(57) ABSTRACT

A new and distinct *K. blossfeldiana*×*K. laciniata.* interspecific hybrid plant named 'JODIE' characterized by a large number of petals per flower resulting in a double-type or multi-petalled trait; the large size of petals resulting in a large flower; a unique soft pink color with a touch of yellow; and a large number of flowers per plant.

3 Drawing Sheets

Botanical designation: *K. blossfeldiana*×*K. laciniata* interspecific hybrid.
Variety denomination: 'JODIE'.

BACKGROUND OF THE INVENTION

The present invention relates to a new and distinct cultivar of *Kalanchoe* plant, botanically known as *K. blossfeldiana*× *K. laciniata* interspecific hybrid, hereinafter referred to by the cultivar name 'JODIE'. As used herein, "interspecific hybrid" includes the progeny from the cross of two different species of *Kalanchoe,* as well as, the progeny resulting from subsequent backcrossing to one of the parents.

The genus of *Kalanchoe* belongs to the sedum family (Crassulaceae). There are more than 100 different species of *Kalanchoe,* of which more than 60 are found growing wild on Madagascar, many in South Africa and a few in Asia and South America. *Kalanchoe* belongs to the succulent plants, which are characterized by watery leaves. The leaves enable them to withstand drought in nature or on the windowsill for a longer time than most other plants, and this allows for a supreme longevity.

The new *Kalanchoe* cultivar is a product of a controlled breeding program conducted by the Inventors, Knud Jepsen and Ellen Christensen, in Hinnerup, Denmark. The objective of the breeding program was to create new *Kalanchoe* cultivars with large flowers, numerous petals per flower, attractive flower coloration and excellent postproduction longevity.

The new *Kalanchoe* cultivar originated from a cross made in a controlled breeding program by the Inventors in Hinnerup, Denmark. The female parent, designated *K. blossfeldiana* cultivar 'Leonardo', is described in pending U.S. Plant Pat. No. 13,365, and having the multi-petalled double-type flower characteristic. The male parent designated *K. blossfeldiana*×*K. laciniata* interspecific hybrid 'KJ 1998-469', unpatented, having very large single-type flowers. The new *Kalanchoe* cultivar 'JODIE' was discovered and selected by the Inventors as a flowering plant within the progeny of the stated cross in a controlled environment in Hinnerup, Denmark.

Asexual reproduction of the new cultivar by vegetative terminal cuttings was first performed in April of 2004 in Hinnerup, Denmark, and has demonstrated that the combination of characteristics as herein disclosed for the new culitvar are firmly fixed and retained through successive generations of asexual reproduction. The new cultivar reproduces true-to-type through asexual reproduction.

BRIEF SUMMARY OF THE INVENTION

The following traits have been repeatedly observed and are determined to be basic characteristics of the new *Kalanchoe* cultivar 'JODIE' which in combination distinguish this *Kalanchoe* as a new and distinct cultivar:

1. a large number of petals per flower resulting in a double-type or multi-petalled trait;
2. the large size of petals resulting in a large flower;

3. a unique soft pink color with a touch of yellow; and 4. a large number of flowers per plant.

Table 1 provides a comparison among plants of 'JODIE' and plants of the parents, *K. blossfeldiana* cultivar 'Leonardo' and *K. blossfeldiana*×*K. laciniata* interspecific hybrid 'KJ 1998-469':

| Trait | New Cultivar 'JODIE' | Female Parent 'Leonardo' (patented, PP13,365) |
|---|---|---|
| Height of cultivar | Is about 25 cm | Is about 30 cm |
| Flower Type | Double-type | Double-type |
| Flower Diameter | 20-24 mm | 15-17 mm |
| Flower number | 250-350 | 250-300 |
| Number of Corolla Lobes | Up to 43 full or partial petals | Between 18-25 full or partial petals |
| Corolla Coloration | Red-purple. Summer coloration: Center of the flower corolla is 65 A. Border of the corolla is 65 D. Fine thin longitudinal line from apex to base (1 mm) with 64 D. Winter coloration: Center of the corolla is 62 A. The border of the corolla is 65 C. Fine thin longitudinal line from apex to base (1 mm) with 64 C. | Red-purple. RHS N74 A with one very thin longitudinal line from apex to base (1 mm) RHS 71 B. |
| Shape of petal | Broadly elliptic petals. The width of the petal is 6 mm and the length is 9 mm. The shape of the apex is cuspidate with entire margin. | Elliptic petals. The width of the petal is 4 mm and the length is 7 mm. The shape of the apex is cuspidate with entire margin. |
| Leaf | Ovate leaves with medium petiole. The apex is obtuse and the base is obtuse. | Ovate leaves with medium petiole. The apex is obtuse and the base is rounded. |
| Leaf texture | The texture of the leaf is glabrous and shining. | The texture of the leaf is glabrous and shining. |

| Trait | Male Parent 'KJ 1998-469' (unpatented) |
|---|---|
| Height of cultivar | Is about 33 cm |
| Flower Type | Single-type |
| Flower Diameter | 20-25 mm |
| Flower number | 350-400 |
| Number of Corolla Lobes | 4 petals |
| Corolla Coloration | Red-purple. RHS 68 B with many fine longitudinal lines RHS 62 D. The border of the corolla is 62 D. |
| Shape of petal | Broadly elliptic petals. The width of the petal is 8 mm and the length is 12 mm. The shape of the apex is cuspidate with entire margin. |
| Leaf | Elliptic leaves with long petiole. The apex is rounded and the base is obtuse. |
| Leaf texture | The texture of the leaf is glabrous and shining. |

Of the many commercial cultivars known to the present Inventors, the most similar in comparison to 'JODIE' is granted *Kalanchoe* cultivar '2002-0504', U.S. Plant Pat. No. 14,908. Comparing these two cultivars, besides the petal color being a different pink shade, the main distinction is that plants of 'JODIE' have large sized petals resulting in large flowers which have a very harmonic symmetry.

BRIEF DESCRIPTION OF THE DRAWINGS

The accompanying photographs illustrate the overall appearance of the new *Kalanchoe* cultivar 'JODIE' showing the colors as true as is reasonably possible with colored reproductions of this type. Colors in the photographs may differ slightly from the color value cited in the botanical description which accurately describe the color of the new *Kalanchoe* cultivar 'JODIE'.

DETAILED BOTANICAL DESCRIPTION

Figure 1:
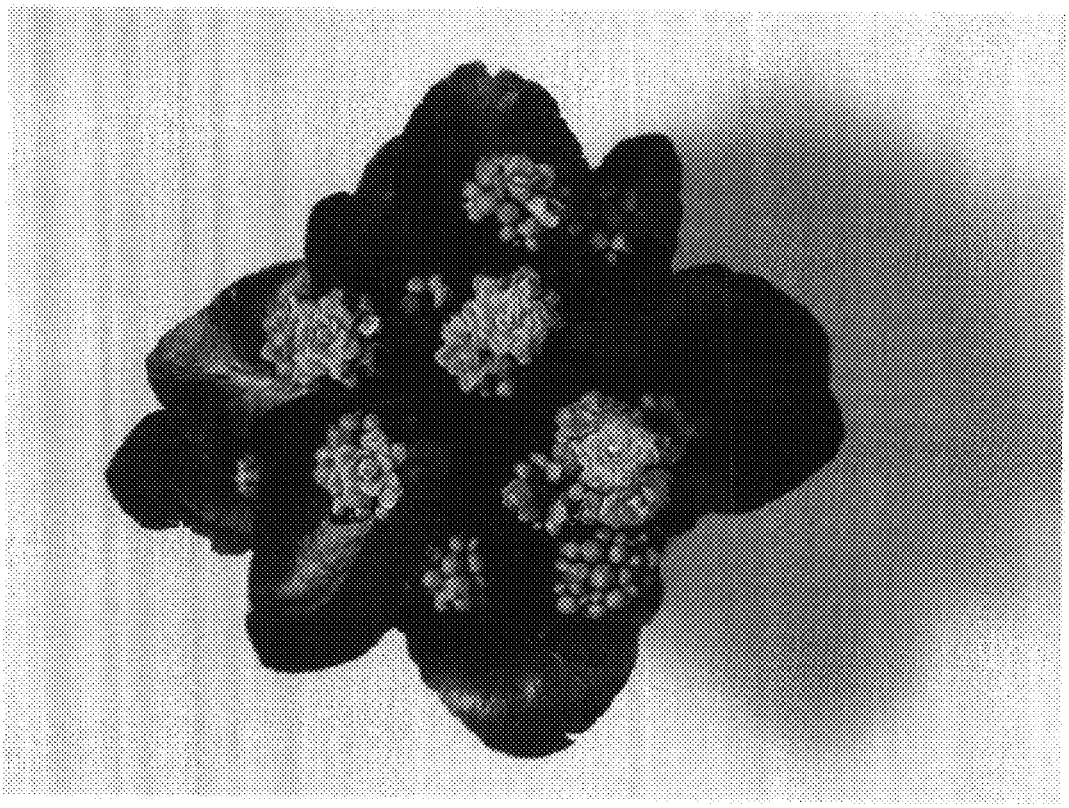
FIG. 1 shows a top perspective view of a typical potted flowering plant of 'JODIE', 19 weeks after planting of cutting.
Figure 2:
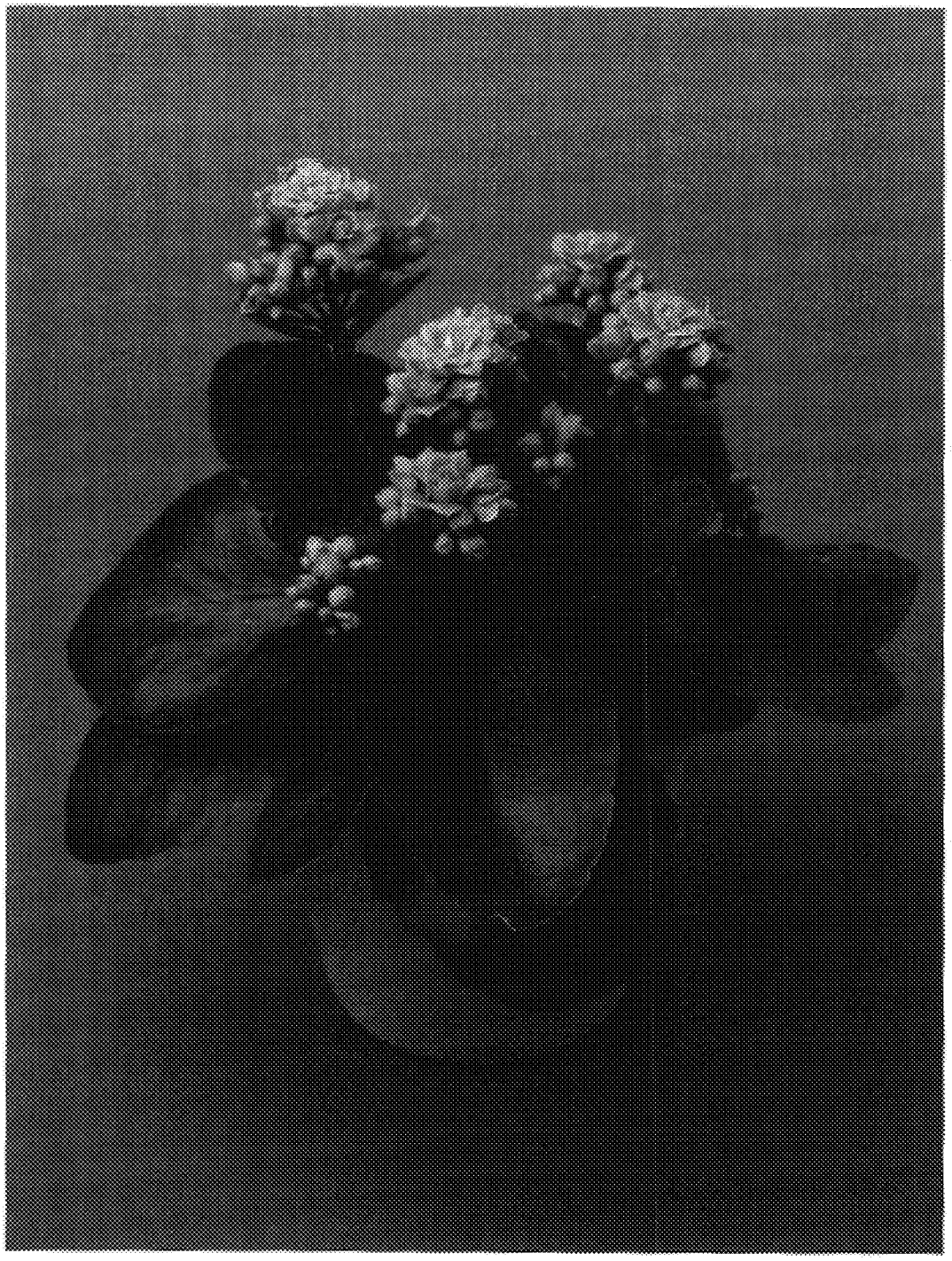
FIG. 2 shows a side perspective view of a typical potted flowering plant of 'JODIE', 18 weeks after planting of cutting.
Figure 3:
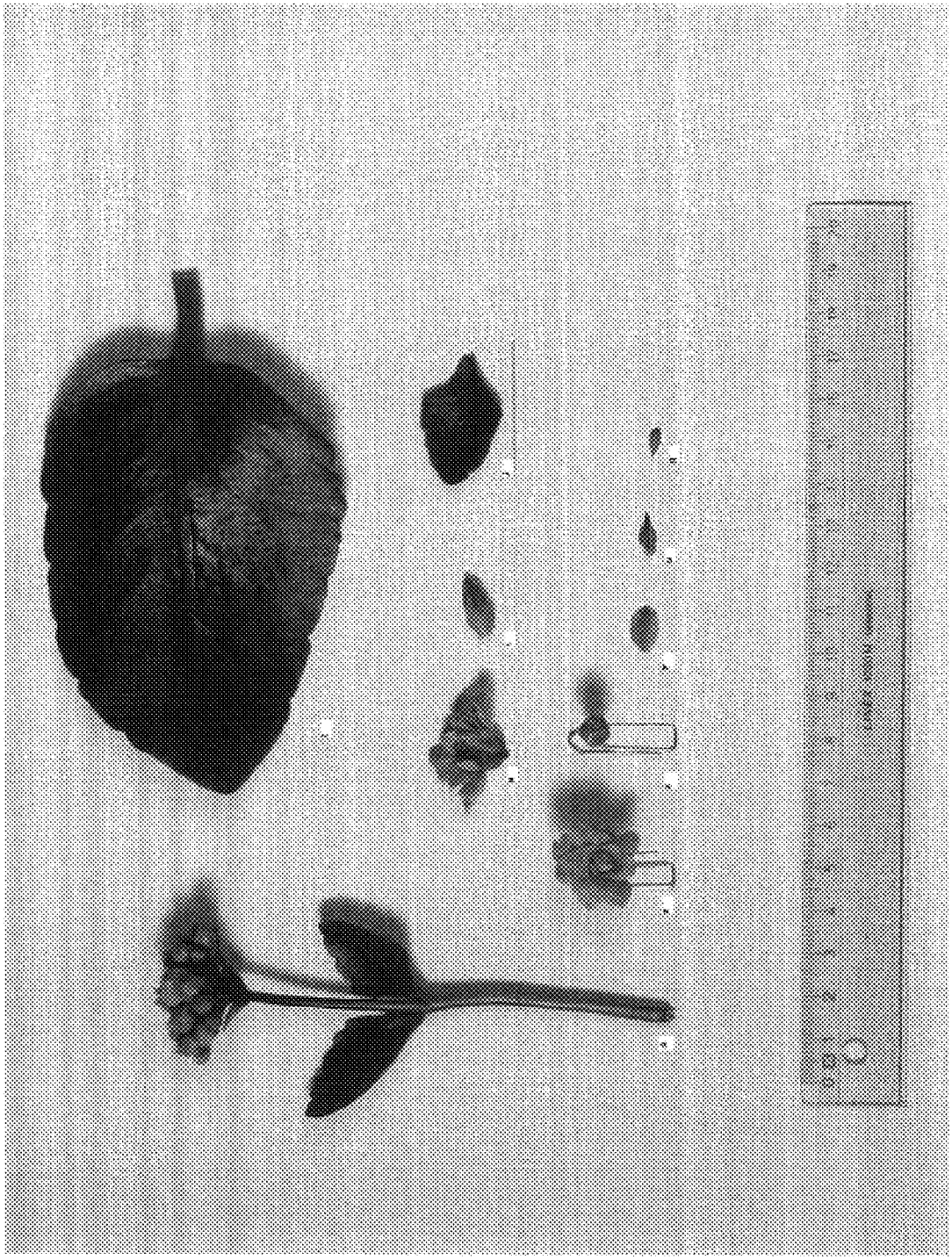
FIG. 3 shows the following typical plant parts of 'JODIE': A. Inflorescence; B. Inside a flower; C. Flower bud, site; D. Flower; E. Flower bud, top; F. Petal; G. Pistil; H. Sepal; I. Mature leaf; J. Young leaf.

The new *Kalanchoe* cultivar 'JODIE' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new *Kalanchoe* cultivar as grown in a greenhouse in Hinnerup, Denmark, under conditions which closely approximate those generally used in commercial practice. The plants were grown in greenhouse at 64.4° F. at daytime and 68° F. during night. The cultivar was produced in a 10.5 cm pot. The cuttings were grown in a long day for the first 5 weeks. From week 6 after planting and onwards, the cultivar was grown in short day conditions (10 hours light and 14 hours darkness). After 17 weeks in total, the cultivar would be ready for sale. The cultivar was grown under natural light conditions supplemented with 70 $\mu mol/m^2/s$ SON-T light when the natural light was less than 100 $\mu mol/m^2/s$. At a short day, the flowering was induced. The reaction time from day of induction to day of first opened flower was 74 days. The peat based soil mix was watered with a solution containing 200 parts per million (ppm) nitrogen, 200 ppm potassium, 40 ppm phosphorous, 200 ppm calcium, 40 ppm magnesium, 60 ppm sulphate, 1 ppm iron, 0.6 ppm manganese, 0.1 ppm copper, 0.1 ppm zink, 0.3 ppm borium, and 0.03 ppm molybdenum.

In the following description, color references are made to The Royal Horticultural Society Colour Chart (R.H.S.), published 2001, except where general colors of ordinary significance are used. Color values were taken under daylight conditions at approximately 12 noon in a greenhouse in Hinnerup, Denmark. The age of the plant described is 19 weeks from the time the cutting was planted in growth medium to when the picture was taken.

Parentage:

*Male or pollen parent.*—*K. blossfeldiana*×*K. laciniata* interspecific hybrid 'KJ 1998 469'.

*Female or seed parent.*—*K. blossfeldiana* cultivar 'Leonardo' (disclosed in U.S. Plant Pat. No. 13,365).

Classification:

*Botanical*—*K. blossfeldiana*×*K. laciniata* interspecific hybrid cultivar 'JODIE'.

Propagation: Vegetative terminal cuttings.

*Rooting habit.*—The cultivar has numerous, branched, fine and fibrous roots.

*Time to initiate roots.*—It takes between 1 and 2 weeks to initiate roots.

*Time to produce a rooted cutting.*—It will take 3 weeks to produce a well rooted cutting. In winter time, it can take on week more.

Plant: If the plants are grown according to the description above, it will perform as described below. Variation from this should be expected over the course of the year, and if the physical growing conditions varies from the description.

*Growth habit.*—This cultivar is upright and uniform. The flowers are formed above the top of the leaf canopy, but the flowers will also appear between the leaves. The flowers are assembled in numerous compound inflorescences. 'JODIE' is freely flowering with numerous compound cymes.

*Growth rate.*—Ready for sale after 18 weeks.

*Branching habit and description.*—Freely branching; typically 8 to 10 lateral branches develop per plant.

*Height at flowering.*—The height of the cultivar is about 25 cm from the bottom of the pot to the top of the plant, depending on the growth conditions.

*Spread/diameter at flowering.*—The diameter of the cultivar at flowering is from leaf tip to leaf tip about 25 cm.

Stems:

*Appearance.*—The cultivar has between 8 to 10 stems with none, one or numerous leaf pairs on the stem. The inflorescence on the top of the flower stem is branched giving an inverted triangle with a rounded crown. Each branch has between 25 and 43 flowers. Aspect: The stem is strong. Length: The length varies from 12 to 16 cm depending on growth conditions. Texture: The texture of the stem is glabrous and shining. Color: The color of the stem is yellow green, RHS 137 A.

Foliage:

*Arrangement.*—The foliage is yellow-green with the same color of the immature as well as the mature leaf, RHS 139 A. The majority of the leaves are at the base of the plant, but immature leaves appear also on the flowering stem.

*Overall shape of leaf.*—The leaves are defined as ovate leaves.

*Apex.*—The form of the apex is acute.

*Base.*—The form of the base is obtuse.

*Length.*—The length of the foliage varies from 5 cm for an immature leaf to 10.5 cm for a mature leaf.

*Width.*—The width varies from 3 cm for an immature leaf to 8 cm for a mature leaf.

*Margin.*—The foliage has a crenate margin.

*Texture.*—The foliage is glabrous and shining.

*Color of upper surface.*—Mature leaf: The color of the mature leaf is a dark green color, and is closely described with RHS 139A. The margin has a brighter green color and is closely described with RHS 144A. Immature leaf: The immature leaf is a dark green color, and is closely described with RHS 139A. The margin has a brighter green color, and is closely described with RHS 144A.

*Color of lower surface.*—Mature leaf: The color of the lower surface is grayish green color, and is closely described with RHS 138A. Immature leaf: The immature leaf is a grayish green color, and is closely described with RHS 138A.

*Venation color.*—Upper surface: No difference between the color of venation and the rest of the leaf. Lower surface: No difference between the color of venation and the rest of the leaf.

*Petiole.*—Length: The length of the petiole varies between an immature and mature leaf. The length of an immature leaf is about 1 cm. The length of a mature leaf is about 3.5 cm. Diameter: The diameter of the petiole varies between an immature and mature leaf. The diameter of an immature leaf is 5 mm. The diameter of a mature leaf is 7 mm. Color: Dark green, RHS 139A.

Flower description:

*Flower type and habit.*—The flower is a double-type with up to 43 petals per flower. The average number of petals per flower is 35.

*Natural flowering season.*—The flowering season is year round, when grown according to description above. When planting outside the flowering season will be in the summer (April to October), depending on local climatic conditions.

*Time to flower.*—The time from start of short day treatment to 1$^{st}$ flower is about 74 days, approximately 1 week longer in winter time.

*Flowering stem length.*—The length of the flowering stem is ranging from 15 to 18 cm depending on the growth conditions.

*Post production longevity.*—'JODIE' maintain good leaf and flower substance for at least 6 weeks under interior environmental conditions.

*Winter hardiness/weather tolerance.*—'JODIE' withstands wind; rain and direct sunlight, and can cope with temperatures between 40 and 95 degrees F.

*Fragrance.*—'JODIE' has no fragrance.

*Flower size.*—The diameter of the flower range from 20 to 24 mm.

*Overall shape.*—The shape is rose-like shape, defined by at least 5 petals per flower.

*Quantity.*—'JODIE' produces a large number of flower ranging from 250 to 350 flowers per plant.

*Bud.*—Rate of opening: From the time when the bud is showing color, the flower will open within 10 days. Color: The color of the bud is yellow green, RHS 144B with a touch of red-purple, RHS 65A. Shape: The shape of the bud is ellipsoidal with the smallest diameter toward the apex/base. Length: The length of the bus is about 1.5 cm. Diameter: The diameter of the bud is about 4 mm at the base and about 7 mm at the top.

*Petal.*—Quantity: Typically 30–35 petals fused at the base. Shape: The shape of petal is broadly elliptic. Length: The length is about 9 mm. Width: The width is about 6 mm. Apex: The shape of the apex is cuspidate. Margin: The shape of the margin can be described as entire. Texture: The texture of the petals is soft, smooth and matte. Color (when opening & fully opened): The coloration of the upper surface of 'JODIE' changes over the year. During summertime the colors are more intense, whereas the winter colors are more dusty. Summer time: Upper surface: The center of the upper surface of the petal has an intense warm red-purple color RHS 65 A. The border of the corolla has a bright red-purple color, RHS 65 D. A fine this longitudinal line from apex to base (wide is 1 mm) with a darker red-purple color, RHS 64 D. Lower surface: The lower surface of the petal is bright red-purple RHS 62 D, with a touch of a darker red-purple, RHS 62 B. Winter time: Upper surface: The center of the upper surface of the petal has a dusty warm red-purple color, RHS 62 A. The border of the petal is 65 C. Fine thin longitudinal line from apex to base (1 mm) with a darker red-purple color, RHS 64 C. Lower surface: The lower surface of the petals is bright red-purple RHS 62 D with a touch of a darker red-purple RHS 62 B.

*Sepal.*—Quantity: Typically 4, fused or non-fused at based. Shape: The shape of sepal is lanceolate. Length: The length is 8 mm. Width: The width is 3 mm. Apex: The shape of the apex is acute. Margin: The shape of the margin is entire. Texture: The texture of the sepals is glabrous and shining. Color when opening: Upper surface: The upper surface of the sepal is yellow green, RHS 143A. Lower surface: The lower surface of the sepal is yellow green, RHS 143A. Color when fully open: Upper surface: The upper surface of the sepal is yellow green, RHS 143A. Lower surface: The lower surface the sepal is yellow green, RHS 143A.

*Peduncle description.*—Length: Every flower has a peduncle with a length of 4 mm. Color: The peduncle is green, RHS 144A. Texture: The peduncle is glabrous and shining.

Reproductive organs:

*Androecium.*—Stamen: Number: The flower has between 4 and 6 stamens. Color: The color of the stamens is yellow-orange, RHS 19A.

*Anthers.*—Number: The number of anthers is between 4 and 6. Size: The size is 1 mm in length. Color: The color of the anthers is yellow-orange, RHS 20B.

*Filament color.*—The color of the filament is yellow-orange, RHS 19C.

*Pollen color.*—The color of the pollen is yellow-green, RHS 15C.

*Pollen amount.*—A very small amount of pollen with pour pollen fertility of 2%, depending on the time of year.

*Gynoecium.*—Regarding the pistil, stigma, style and ovary abnormality of can occur, and a part of the female reproduction organs will not fully develop. Pistil: Number: The number of pistils is 3–4. Stigma: Shape: The shape of stigma is round. Color: The color of the stigma is green, RHS 145 C. Style: Shape: The shape of the style is thin and cylindrical. Color: The color of style is green, RHS 145 C. Ovary: Color: The color of ovary is green, RHS 144 C.

*Seeds.*—Number: Between 20 and 30 potential seeds per ovary. Width: The width of the seeds is less than 0.5 mm. Length: The length of the seeds is less than 1.0 mm. Shape: The shape of the seeds is ellipsoidal. Color: The color of the potential seeds is yellow-green, RHS 145 B.

*Fruit* (*ovary*).—Shape: The shape of the fruit is cylindrical. Width: The width of the fruit is 1.5 mm. Length: The length of the fruit is 3 mm. Color: The color of the fruit is green, RHS 144 C.

Disease resistance/susceptibility: No information on disease resistance or susceptibility is currently available.

Pest resistance/susceptibility: No information on pest resistance or susceptibility is currently available.

We claim:

1. A new and distinct *K. blossfeldiana*×*K. laciniata* interspecific hybrid plant named 'JODIE', substantially as illustrated and described herein.

* * * * *